United States Patent [19]
Cook

[11] 4,422,185
[45] Dec. 27, 1983

[54] WELDING HELMET

[76] Inventor: Reuben E. Cook, Box 600, Loup City, Nebr. 68853

[21] Appl. No.: 158,368

[22] Filed: Jun. 11, 1980

Related U.S. Application Data

[63] Continuation-in-part of Ser. No. 836,516, Sep. 26, 1977, abandoned.

[51] Int. Cl.³ .............................................. A61F 9/06
[52] U.S. Cl. ........................................................ 2/8
[58] Field of Search ............................ 2/8, 10, 11, 421

[56] References Cited

U.S. PATENT DOCUMENTS

| | | | |
|---|---|---|---|
| 1,944,399 | 1/1934 | Bowers | 2/8 |
| 2,511,234 | 6/1950 | Anderson | 2/8 |
| 2,550,575 | 4/1951 | Malcom | 2/8 |
| 2,747,191 | 5/1956 | Hoffmaster | 2/8 |
| 2,761,046 | 8/1956 | Herrick et al. | 2/8 X |
| 3,041,622 | 7/1962 | Gurtowski | 2/8 |
| 3,257,667 | 6/1966 | Anderson | 2/8 |
| 3,325,824 | 6/1967 | Donegan | 2/8 |
| 3,339,207 | 9/1967 | Perry | 2/8 |
| 3,368,220 | 2/1968 | Wezel | 2/8 |
| 3,430,262 | 3/1969 | Raschke | 2/8 |
| 3,458,865 | 8/1969 | Simpson et al. | 2/8 |
| 3,490,071 | 1/1970 | Marshall | 2/8 |
| 3,517,392 | 6/1970 | Hodge et al. | 2/8 |
| 3,577,563 | 5/1971 | Raschke | 2/8 |
| 3,775,774 | 12/1973 | Herman | 2/8 |
| 3,838,247 | 9/1974 | Finger et al. | 2/8 X |
| 3,868,727 | 3/1975 | Paschall | 2/8 |
| 4,011,594 | 3/1977 | Guilbaud et al. | 2/8 |

*Primary Examiner*—Werner H. Schroeder
*Assistant Examiner*—Andrew M. Falik
*Attorney, Agent, or Firm*—Hiram A. Sturges

[57] ABSTRACT

A welding helmet comprising a face protective hood, a head-band, the hood pivoting on the head-band upwardly and downwardly, and a stop assembly for stopping the hood from pivoting downwardly beyond a position in which its viewing opening is in a position for sight. A dark plate carrying visor is located in front of the hood and mounted on the hood for swinging upwardly and downwardly, the visor having a wide swinging arc so as to stay closer to the hood when raised. The stop assembly has two portions attached-one to the hood and one to the head-band through a hard hat, or more directly to the head-band when a hard hat is not used, the chain strap being resiliently and adjustably held in position, and the top of the hood being corrugated for stiffness.

28 Claims, 27 Drawing Figures

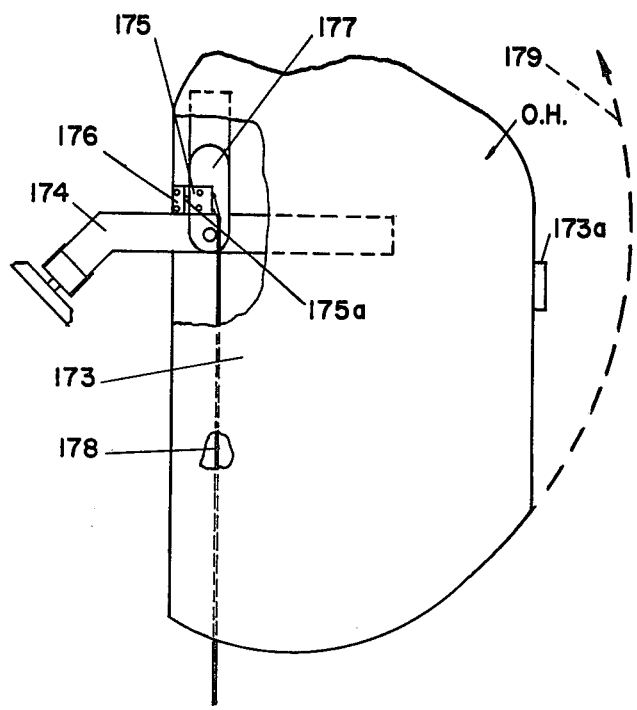
FIG. 9
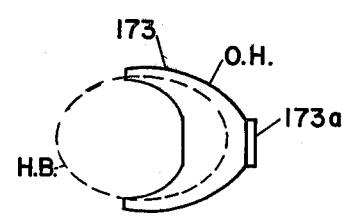
FIG. 9A
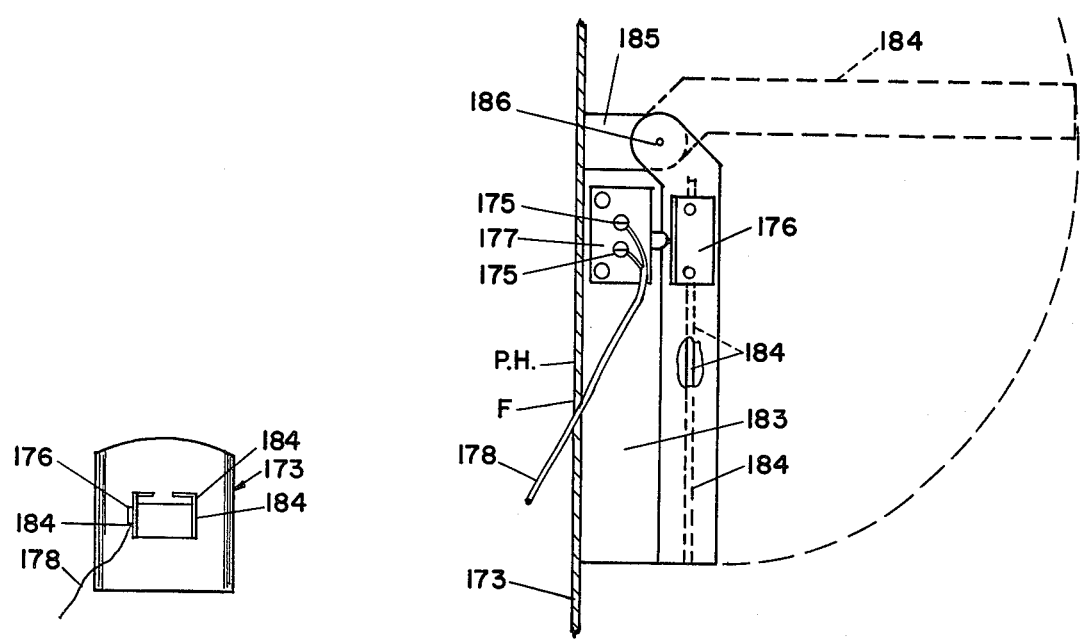
FIG. 10A
FIG. 10

WELDING HELMET

This application is a continuation-in-part of the applicant's earlier application Ser. No. 836,516 filed Sept. 26, 1977 and titled: Welder's Helmet.

BACKGROUND OF THE INVENTION

This invention is in the field of welding helmets of a type having a hood in front of a head-band in which the hood has a clear plate lens and further in which a dark plate is mounted on a pivoting visor in front of the clear plate lens.

It had been common for such visors to pivot at their top edge upwardly and outwardly from the hood. Pivoting much farther rearwardly is an objective hereof so as to permit a raised visor to be much closer to the hood for clearance in right places, especially when a large window is desired.

Another problem has been the falling of a hood downwardly out of position by pivoting due to gravity and an objective assembly hereof having a portion on the hood and a cooperative portion on the head-band or on a hard hat fixed there to prevent this.

Another problem has been the need to keep the chin strap on the chin as the chin moves downwardly and rewardly in an arc, and it is an objective hereof to resiliently urge the chin strap rearwardly to keep it on the chin.

BRIEF DESCRIPTION OF THE DRAWING

FIG. 1 illustrates a head band in use with the helmet.

FIG. 1B is a view of a pivot assembly on the left side of the helmet as it would be seen from the rear and with the rear half of cooperating parts removed for exposing the screw, portion of the helmet rearwardly of the screw being removed and portions of a head band and of a hard hat are shown in cross-section.

FIG. 3 shows only parts of the main modification which is FIG. 1, and also shows the position of the dark plate of the visor, a protective clear plate in front of the dark plate and a clear plate of the helmet. A releasing position of a rotating locking device for locking a clear viewing plate of the hood and its gasket in place is shown in dotted lines at the left in FIG. 3, with the full lines showing its locking position.

FIG. 9 shows the electrical components with the necessary wiring diagram.

FIGS. 10, 11 and 12 illustrate a method of using the suspension similar to that used in a hard cap but using it without the hard cap, thus allowing the operator to use a very comfortable head gear without the weight of a hard cap in areas where a hard cap is not required. This head gear is fitted to the helmet exactly as if the hard cap were still being used.

FIG. 13 is a cross-section taken along the line 13—13 of FIG. 12.

FIG. 17 is a view of FIG. 18 as it would be seen from the left hand side.

DESCRIPTION OF THE PREFERRED EMBODIMENT

Figure 1:
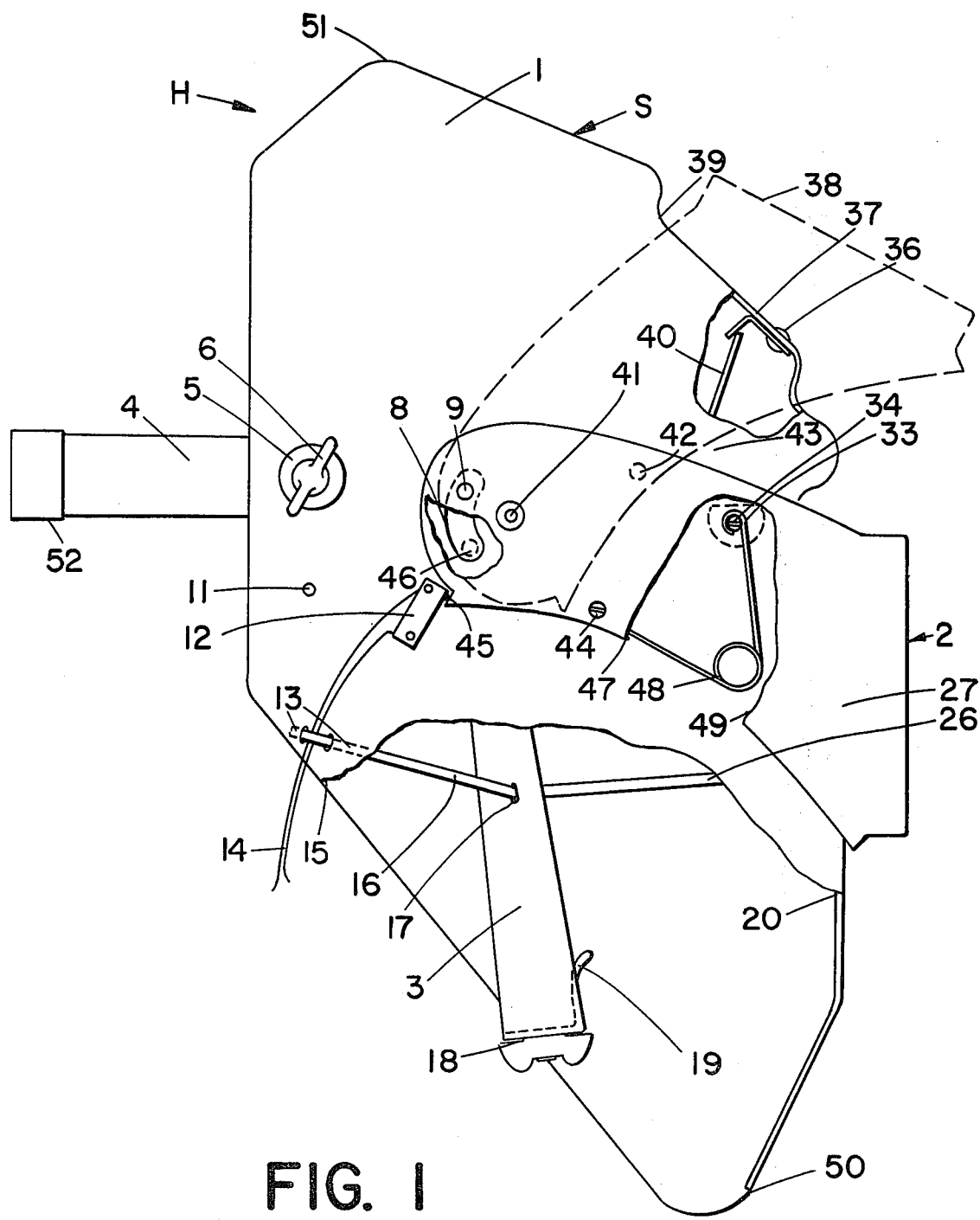
FIG. 1 is a right side elevation of the helmet of this invention with portions of the upper and lower parts of the hood broken away to show inner parts, a visor being shown in lowered position in full lines with a portion broken away and being shown in an upper position in dotted lines.

In FIG. 1 the welding helmet of this invention is generally indicated at H in FIG. 1 and has a hood S also called a face shield, having a body 1 which is closed through its forward side except for a viewing window 80 later described.

The back portion of the hood, as seen in FIG. 1, is open from bottom 50 to top 51 to allow entrance of the operator's head. A visor 2 extends around right and left sides and across the front of the hood S and is fastened to the hood S by pivot bolts 41, disposed one on the right side and one on the left side of the shield.

Figure 2:
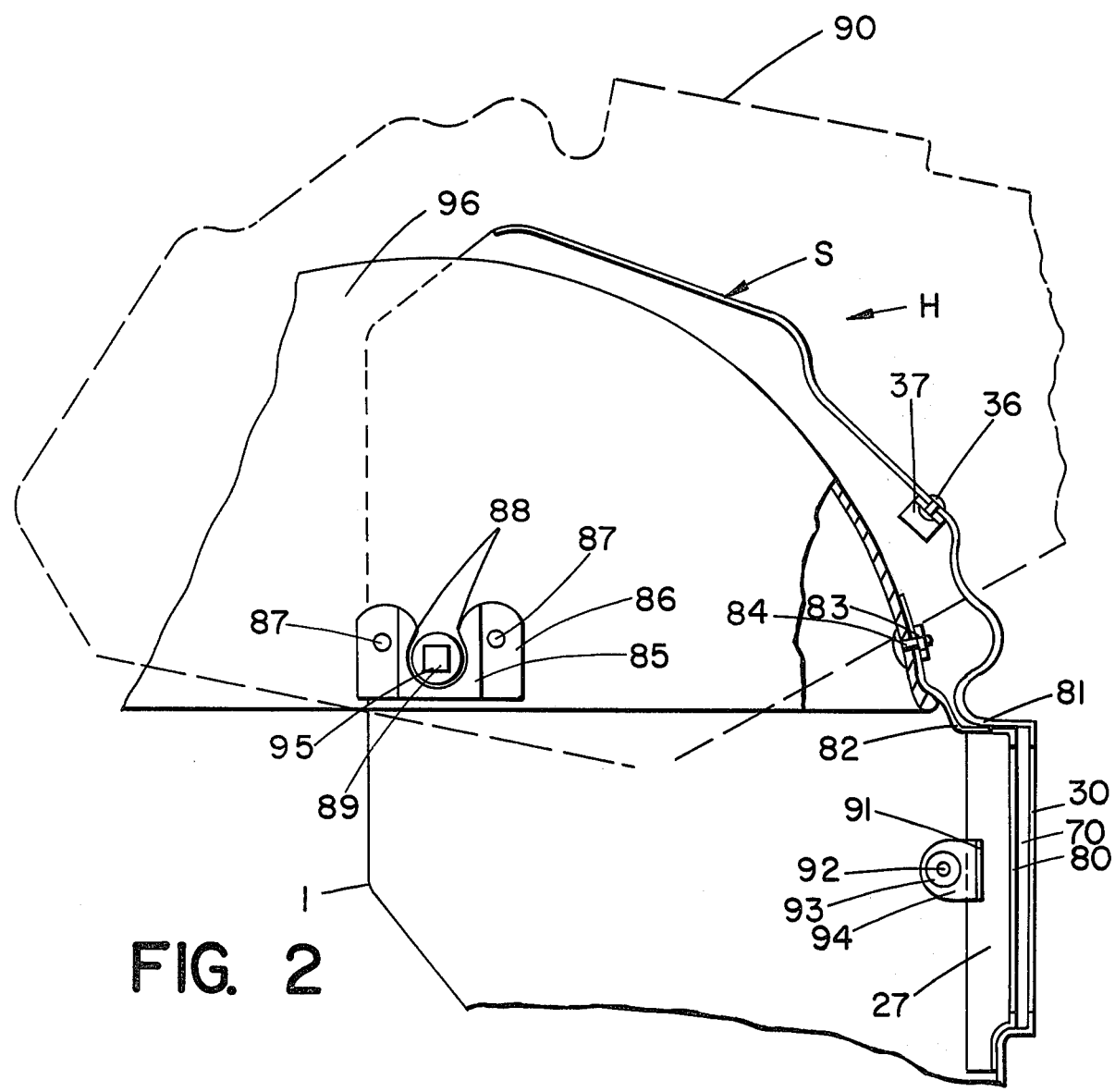
FIG. 2 is a right-side elevation of a helmet of the same modification as FIG. 1, with the single exception that FIG. 2 has a hard cap in place of the head band, the right half of the hood being broken away for showing the hard cap in full lines. A forward portion of the hard cap itself and a large rearward portion of the hard cap being broken away, the hood being shown in a forward position with respect to to the hard cap in full lines and being shown in a raised position with respect to the hard cap in dotted lines, lowermost portions of the hood being broken away in both the full-line and dotted-line illustrations of FIG. 2.
Figure 3:
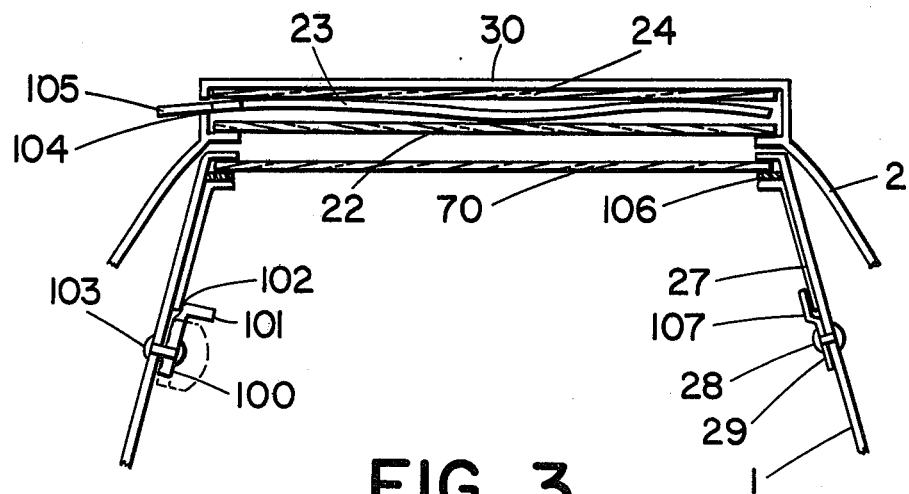
FIG. 3 is a sectional view taken along the line 3—3 of FIG. 2 except that the visor is in the downward position of FIG. 1, whereby all parts shown in FIG. 3 are parts of the main modification of FIG. 1, showing the positions of dark plates and retainers.

As seen in FIG. 2, the visor 2 has a viewing window opening 80 in the hood S. The visor 2 contains, as seen in FIG. 3, a dark plate 22, a clear cover plate 24 forwardly of the dark plate 22, and a spring divider 23 between the plates 22 and 24.

The divider 23 is contoured to maintain a constant pressure on the two plates 22 and 24, keeping them in place.

Figure 7:
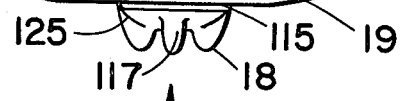

In FIG. 1 a chin strap 3 has a length adjustable to the operator's chin vertically by turning an adjusting nut 18, best seen in FIGS. 4 and 7, the nut 18 lengthens or shortens the side straps 17, as shown in FIG. 7 through a rachet mechanism generally indicated at 18' in FIGS. 4 and 7, and later described.

As seen in FIG. 1, the chin strap 3 has a generally vertical right side portion 3a which has a rest position maintained by a right rubber band 16. The chin strap 3 is adjustable horizontally by moving the position of a rubber band 16 through an opening 17 where it is held in place by friction of the rubber against the sides of the opening 17'.

A head band 4, seen in FIG. 1, is adjustable to the head size of an operator by a rachet mechanism 52 similar to the rachet mechanism 18. The head band 4 has an adjustable arch band 7 which is an integral part of the head band 4.

The head band 4 can also be called a hood-to-head attaching assembly 4 and it has in it a head-receiving opening 51' having a head-engaging surface (53) for engaging the head of the operator; the surface 53 having a rearwardmost portion 54'.

The rearward end 13 of the rubber band 16 is fixed to the face shield 5 in any suitable way at a point 16a, and spaced mostly rearwardly but slightly upwardly from the position of the slot 17 when the chin strap 3 is in a relaxed position with the visor 2 in the down position of FIG. 1. The rubber band 16 extends mostly forwardly but somewhat upwardly form the position of the slot 17 when the visor is down, the forward end of the chin strap 16 being suitably attached to a part of the helmet which is stationary with respect to the face shield 5, such as the retainer 27, as seen in FIG. 2.

Figure 1A:
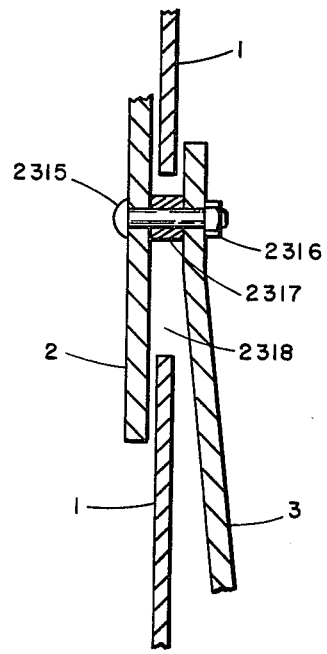
FIG. 1A is a cross section through 1A—1A of FIG. 1 showing a helmet, a chin strap and a slot which allows the movement of the chin strap. A visor, a spacer, bolt and self-locking nut are also shown.
Figure 1B:
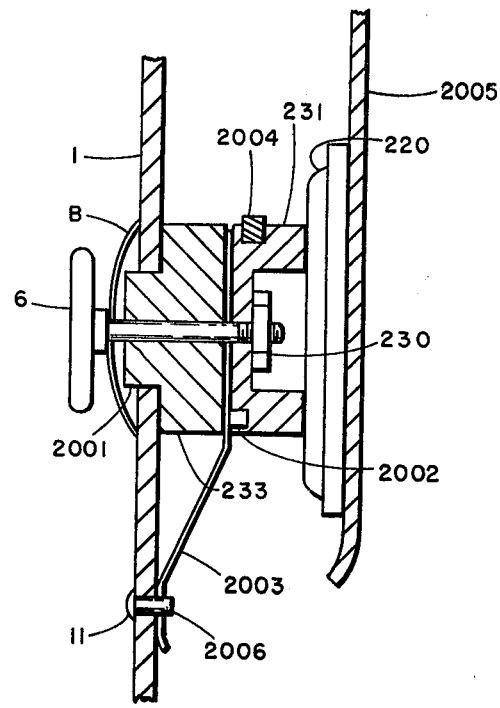
FIG. 1B applies to the FIG. 2 hard hat embodiment in which a hard hat is received inside the head band of FIG. 12.

Referring to FIGS. 1 and 1B the head band assembly is attached to the face shield by means of prior art type attachment assemblies 6' on either side of the helmet, each having a square shoulder 2001 which passes through a square hole 2001' in the side of the face shield, as seen in FIG. 1B. This attachment assembly 6' also contains a friction washer B which can be adjusted for any desired tension by adjusting the thumb screw 6 against the washer B, putting progressive tension on the remainder of the attachment assembly 6' of the helmet. The assembly on one of the sides also contains a stop lever 2003 which acts as a part of the stop when the face shield is pivoted up over the head of the operator. A similar head-band and stop is used by most helmet manufacturers.

A new and different adjustable stop 40 is riveted to the front of the head-band at 43 and rests against a striker 37 which is fastened to the inside of the face shield by a rivet 36. When a hard cap is used with the helmet instead of the head-band, the striker 37 just be pivoted 90 degrees so that it will not interfere with the hard cap.

After the operator has fitted the helmet to his head and chin, a downward pressure of his chin will cause the chin strap to be lowered causing a connecting bolt 9 to pull downward on the back end of the visor to which it is fastened through a slot 8 in the face shield.

A spring 48 is fastened to the inside of the visor by a pivot bolt 44 and is also fastened to the face shield by a pivot bolt 34. The bolt 34 is held in place by a nut on each side of the face shield thus allowing the spring to pivot but holding the bolt 34 in place. The bolt is adjustable in a slot 33 to allow adjustment of the spring tension.

As the visor begins to move upward, the striker 45 moves away from the switch 12 breaking the electrical contact inside of the switch and shutting off the welding machine. This protects the operator's eyes from accidental arc burn.

The downward pressure of the chin strap causes an inward pressure to be exerted on the attaching bolt 9 which in turn puts pressure on the pivot bolt 41 causing an inward pressure to be exerted on the hood 1. To counter-act this pressure and to maintain the flat surface of the area around the viewing window in the hood, two arcuate corrugations 32 and 35 are molded into the front of the top of the hood and extend around the convex curvature of the top of the front of the hood to a point above the pivot bolt 41 and add great structural support to the hood to prevent a buckling inwardly of the sides of the hood under chin strap pressure.

As the operator applies more pressure to the chin strap, the visor will move farther upward to a "line-up point" where the spring pivot bolt 44 is directly in line with the visor pivot 41 and with the stationary bolt 34.

At this "line-up point", if the operator wishes to allow the visor to return to a closed position, releasing the chin pressure will freely allow the visor to return downward where it will be held firmly closed by the spring 48. However, if the operator wishes to move the visor to the extreme open position after reaching this "line-up point", any additional pressure on the chin strap will cause the visor to continue to raise, which causes the spring pivot bolt to raise above a line between the bolt pivot 9 and the bolt 34 and the spring will then begin to exert an upward pressure on the visor and will cause it to raise to the maximum height where it will be held by the spring until a nod of the operator's head or a push with his hand will cause the spring pressure to be overcome so that the hood moves. A depression 39 is molded into the front of the hood S to receive the visor when it is in the fully raised position.

Referring to FIG. 3, when the visor 2 is in the raised position with the viewing window in the hood S uncovered, the operator's eyes are still protected from flying chips by a clear viewing plate 70 fixed to the hood S.

The plate 70 is held in place by a retainer which encircles the viewing window in the hood S, lending strength to that portion of the hood S.

In addition, the retainer serves as an anchor for the forward end of the rubber band 16, as seen in FIG. 2, where the band passes through a slot 26. The retainer is held in place by a contoured strap 29 riveted to the inside of the hood at 28 and held on the opposite side of the hood by an eccentric fastener to facilitate easy removal.

1A is a cross-section through 1A—1A of FIG. 1, and shows a helmet at 1, a chin strap 3. In FIG. 1 slot 8 allows for the movement of the chin strap and the same slot is numbered 2318 in FIG. 1A.

Figures 14, 15:
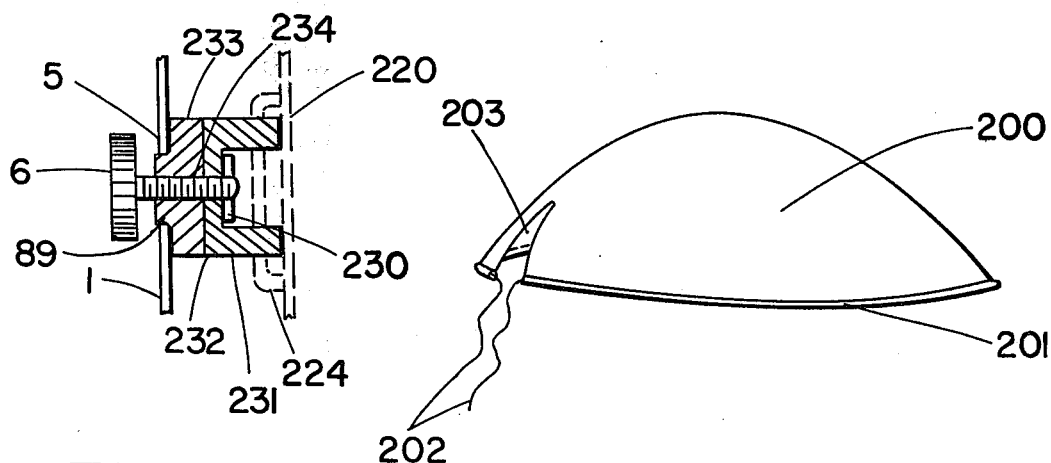
FIG. 14 is a view of a pivot assembly on the left side of the helmet as it would be seen from the rear, and with the rear half of cooperating parts removed for exposing the screw, portions of the helmet rearwardly of the screw being removed and portions of a hard band and of a plate being shown in dotted lines.
FIG. 15 shows a cap in perspective view made of fire resistant cloth.

FIG. 1B is a view similar to FIG. 14, and a hard cap 2005 has a socket 220 cemented to it.

A member 231 slides downwardly into the throat of the socket 220 where it is held in place as later described. An arm 2003 has a series of holes 2006 in line with a rivet 11 to allow for adjustment. A square shoulder 2001 is an integral part of a fixture 233 and fits into a square hole in the helmet.

An arm 2003 has a projection 2002 which rotates upward when the helmet is raised and strikes a projection 2004, which limits the backward movement of the helmet. Desired friction is obtained between the fixture 233 and the member 231 by a threaded bolt pressing on a washer B, causing pressure between the member 231, the fixture 233 and the arm 2003.

Figure 11:
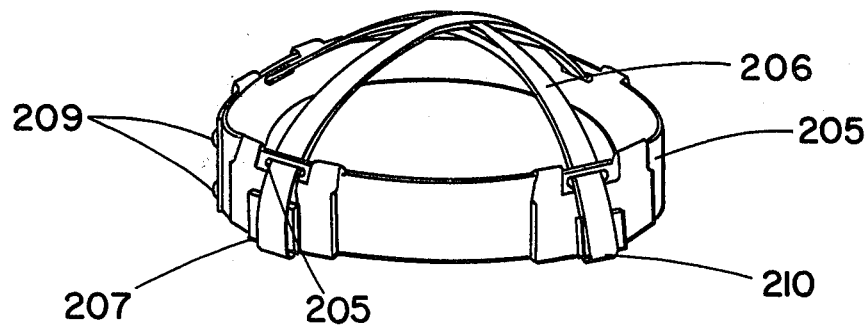
Figures 12, 13:
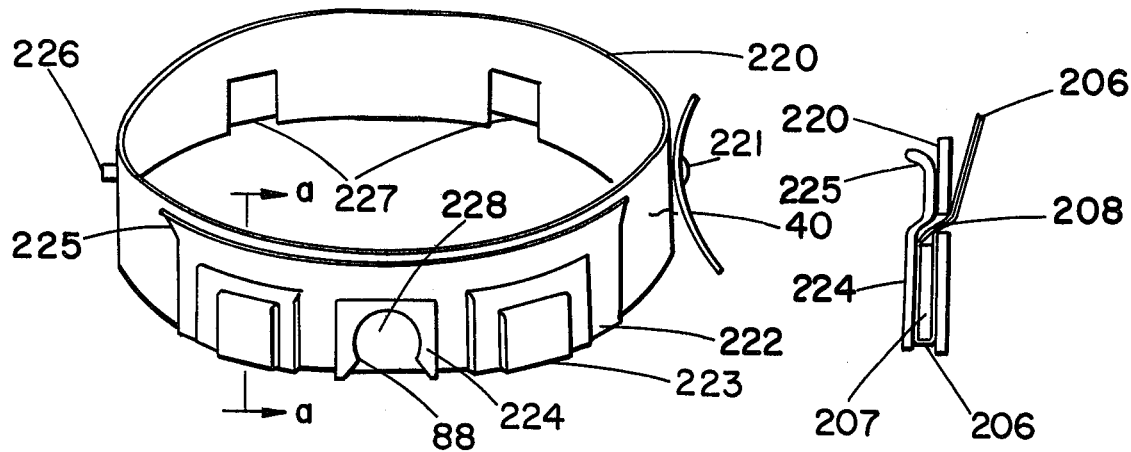

In changing from hard cap use to head-band use, as in FIG. 11, the hard cap is removed by sliding it downwardly out of the throat of the pivoting assembly and sliding the head-band into the fixture 224 for maintaining it in place through the throat 88 in FIG. 12. The flange on the base of the member 231 is shown in dotted lines at 493 in FIG. 17.

FIG. 2 is a side view of the face shield which is cut away to show a hard cap in position within the helmet with the portion of the helmet below the viewing window deleted. No. 1 is the face shield which fastens to the hard cap by pivotal means. The pivot assembly is held to the hard cap by plate 86 which is fastened to the hard cap by bolts 87 passing through the hard cap shell and the plate. The plate is molded with a U shape protrusion 85 which accepts the shoulder on the pivot assembly through throat 88. This throat is made slightly narrower than the body of the pivot assembly so that the pivot is held firmly in place but can be removed by forcing the assembly upward through the throat and thus the helmet can be removed from the hard hat easily. The pivot assembly contains a sqaure washer which protrudes outward from the assembly, through the face shield where a compression washer and a threaded thumb screw hold the face shield to the pivot assembly and where the tension of the assembly washers can be adjusted by tightening the thumb screw.

No 27 is a retainer which holds the inner clear shield in place over the viewing window, No 30. The retainer is held in place by a plate on one side mentioned in FIG. 1 and on the other side by an eccentric plate 94. The eccentric is indented as shown at 93 and pivots around rivet 92 which passes through the face shield and through the plate. A lip 91 stands out away from the face shield and provides a convenient finger hold to facilitate turning the plate and thus removing the retainer so that the clear plate 70 can be removed or replaced.

A stop 82 is provided to keep the hard cap from rotating too far and to keep the viewing window in the proper place in in relation to the operator's line of sight. The stop fastens to the forward area of the hard cap by a bolt which passes through a hole in the hard cap 84 and a knurled nut 83. Stop 82 is slotted where the bolt passes through it so that an adjustment of the height of the viewing window can be made. The stop strikes the face shield just above the viewing window at 81. Stop 37 which is used on the plain head band is turned 90° so that it will not interfere with the movement of the hard cap. It is pivoted on rivet 36.

Dotted line 90 illustrates the position of the face shield when it is in the fully raised position.

FIG. 3 is a bisected view of the front portion of the face shield and visor. No. 1 is the face shield with clear viewing plate 70 in place backed by gasket 106 which completely encircles the plate. This gasket can be removed and replaced by a welding plate of a proper shade for use in gas welding and then the helmet can be used for both gas and arc welding intermittently. Viewing plate and gasket 106 are held in place by retainer 27a which is held in place on the right side by contoured plate 29 held in place by rivet 28. On the left side it is held in place by eccentric plate 100 which is held in place by rivet 103 and which can be pivoted on the rivet by grasping finger hold 101 and turning 180° where retainer 27a can be removed.

No. 2 is the visor with viewing window 30 covered by clear plate 24 and welding plate 22 which are held in place by contoured spacer 23. Both plates and the spacer are inserted into the visor through slot 104. A portion of spacer 23 is left protruding from slot 104 and can be grasped at 105 for easy removal. Spacer 23 is U shaped with the right side open so that the plates will not be scratched when spacer is inserted. The contour of spacer 23 is such that it provides for different thicknesses of plates which may be used.

Figure 4:
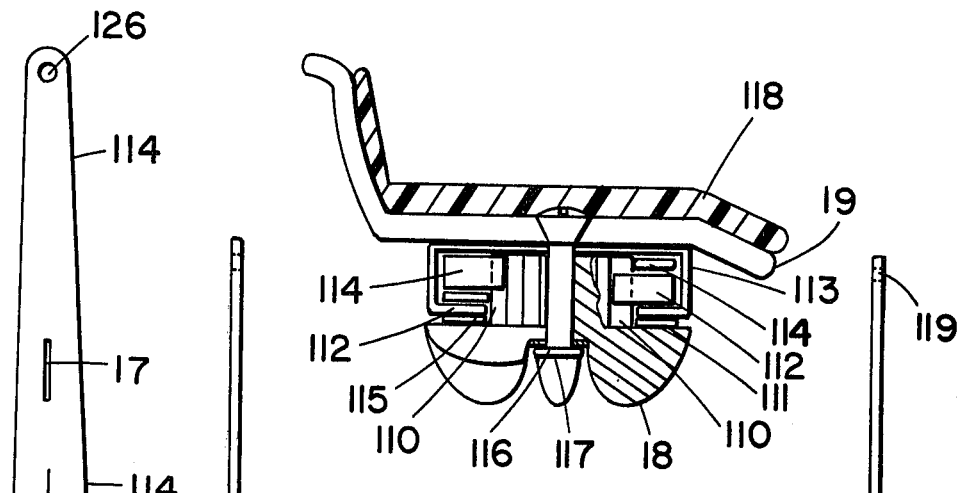
FIG. 4 illustrates the construction of the chin strap with the adjusting mechanism.

FIG. 4 is a drawing of the adjusting mechanism on the chin strap. It is a bisected view through 4—4 in FIG. 7. No. 19 is the spreader which supports the chin pad 118 and is attached to the housing which contains the adjusting device by rivet 117. The housing is No. 113. No. 18 is the adjusting knob and gear with teeth represented at 110. These teeth engage the teeth in the chin straps 112 and 114 on opposite sides of the housing which has the effect of either lengthening or shortening each strap depending upon which direction the knob is turned. The side of the chin strap which engages the gear is made heavier than the opposite side in the case of both straps as is shown in the drawing. A tension washer 111 fits between the housing and the adjusting knob and creates enough friction to assure that the knob will hold the load of the chin pressure but still can be adjusted by hand. No. 116 is a washer which protects the knob from wearing on the end of the rivet 117.

Figure 5:
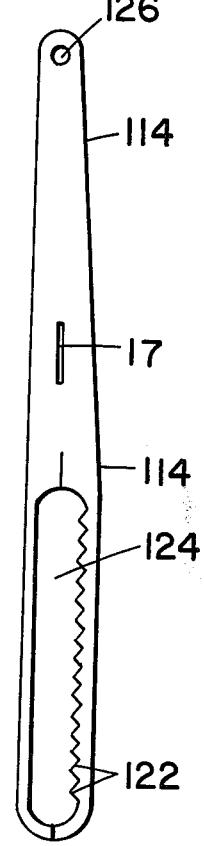
FIGS. 5 and 6 illustrate the side bands of the chin strap.
Figure 6:
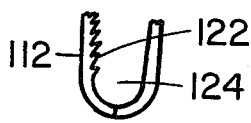

FIGS. 5 and 6 are drawings of the identical chin straps 112 and 114 showing the heavier construction through the tooth section as represented at 123. The teeth are 122 and 124 is the slot in which the gear sets. No. 17 is the slot through which the rubber band travels and No. 126 is the hole through which the attaching bolt passes.

FIG. 7 is a drawing of the entire chin strap assembly as it would look from the back of the helmet. The entire assembly is No. 3 with 121 being the spreader which is made wide enough to accommodate the operator's glasses when the hood is pivoted upward over the head or lowered to working position. Straps 112 and 114 pass through slots in the spreader at 120, then proceed downward and inward to enter the housing directly above adjusting knob 18. Indentations 125 in the top of adjusting knob 18 engages washer 115 causing sufficient friction to maintain the position of the chin straps. No. 9 is a chin pad provided for the comfort of the operator and it is cemented to the central portion of spreader 121. No. 17 shows the slot with rubber band 16 passing through it.

Figure 8:
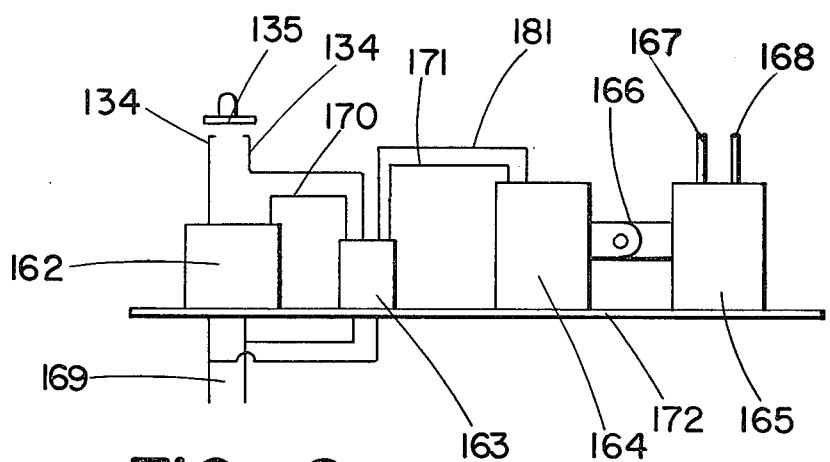
FIGS. 7 and 8 illustrate the method of attaching the protective device to existing helmets.

FIG. 8 shows the components of the electrical safety system as used on either an ordinary transformer or direct current type of welder. The 110 volt leads 169 are connected to a 110 volt plug, not shown, and they furnish current to energise a transformer 162 and a relay 163.

The 24 volt current produced by the transformer is carried by lead 134 to the helmet switch 135 shown in the open position. When the switch closes, current continues through the lead 134 to the relay 163, with the lead 170 completing the circuit. The closing of the switch 135 causes the relay 163 to make contact and send current to the solenoid 164 through the conductors 171 and 181.

When the solenoid 164 is energised, it actuates the switch 165 by a movement of the connecting link 166. Closing the switch 165 closes the welding circuit since leads 167 and 168 connect to the rod holder and to the welder respectively.

The whole assembly is attached to the base 172. When the switch 135 is opened by an upward movement of the helmet visor, the circuit is broken to the leads 167 and 168 and the rod holder, not shown, is inoperable, thus protecting the operator's eyes from an accidental arc.

FIG. 9 is a drawing of an ordinary welding helmet, O. H., showing a side view with a cut away portion showing the head band 174 and the means of attaching the helmet switch to it. 173 is the face shield with plate holder 173a on the front side.

The striker plate 176 is attached to the face shield in a position where it strikes against an operating lever or button 175a of switch 175 when the face shield is in the lowered position. The switch 175 is attached to the head band 174 and when the face shield 173 is rotated upward, the striker plate 176 releases the switch button or lever 175a causing a break in the welding circuit. The lead 178 of FIG. 9 consists of two conductors which lead to the conductors 134 of FIG. 8.

FIG. 9A is a view looking downward on the helmet, O. H. of FIG. 9, with the 173 being the face shield, H. B. representing the head band and 173a the plate holder.

FIG. 10 is a drawing of a popular type of helmet, P. H., in common usage which has a trap door 183 in place of a stationary plate holder. The trap door fastens to the frontal portion of the helmet and is hinged at the top so that the operator need not rotate the entire face shield in order to remove the welding plate from his line of vision. Instead, the trap door can be swung upward as indicated by the dotted line in FIG. 10. Since striker plate 176 is attached to the trap door 184 when the trap door is raised, the striker plate breaks contact with switch 177 which is fastened to the face shield, thus breaking the electrical contact to the rod holder. No. 173 is the forward section of the face shield and 178 is the conductor which connects to the electrical assembly shown in FIG. 8. FIG. 10A is a frontal view of the trap door helmet showing the position of trap door 184, striker plate 176 and shield 173.

FIG. 11 is a drawing of a suspension system used in a popular make of hard-cap. The headband 205 is made of soft plastic material which surrounds the operator's head and is adjustable by movement of adjusting buttons to different slots in the band. Two straps 206, cross over the top of the operator's head, then pass through slots 208 under connector block 207.

FIG. 12 is a band of hard plastic 220 which has been substituted for a hard cap so that the suspension system shown in FIG. 11 may be used with the welding helmet when a hard cap is not necessary or desired. A substantial difference in weight is thereby obtained which enhances the comfort of the operator. FIG. 12 shows cavities 227 which are formed by cover plate 222 which is held to band 220 by cementing or riveting. Plate 222 has formed pockets at 223 which engage connector blocks 207, FIG. 11, and another pocket 228 which has a circular opening to allow insertion of pivot assembly, FIG. 14.

Throat 88 is narrower than the body of the pivot assembly causing the pivot assembly to be held in place during normal useage but also allowing the operator to remove the pivot assembly by exerting a downward pressure on the pivot assembly and forcing the throat to become wider.

40 is an adjustable stop held in place by rivet 221. It is adjusted by rotation.

226 is a protruding rivet and 225 is a flange extending around the upper perimiter of plate 222.

FIG. 13 is a cross-section through a—a' showing the connector block 207 in place in pocket between band 208 and plate 224 and showing band 206 encircling the connecting block.

FIG. 14 is a cross-section of the pivot assembly showing the adjusting screw 6, threaded into square shoulder 89 which is connected to inner nut 230 by threaded tube 234 making the three parts one assembly. Screw 6 depresses tension washer 5 against face shield 1 thus causing friction washer 233 to engage friction washer 231 at 232. 231 has a flanged portion which sets into pocket 228, FIG. 12.

FIG. 15 illustrates a cap made of fire resistant cloth which covers the hard band, FIG. 12, by passing under flange 225, FIG. 12, under rivet 226 and on around the circumference of hard band 220. It is held in place by a tie in the ends of the draw-string 202 which passes through sleeve 201 which encircles the lower perimiter of the cap 200. A small gap is left at 203 to allow for any deviation in the size of the hard band. This cap affords protection for the operator's head from flying sparks and chips while wearing the helmet.

Figure 16:
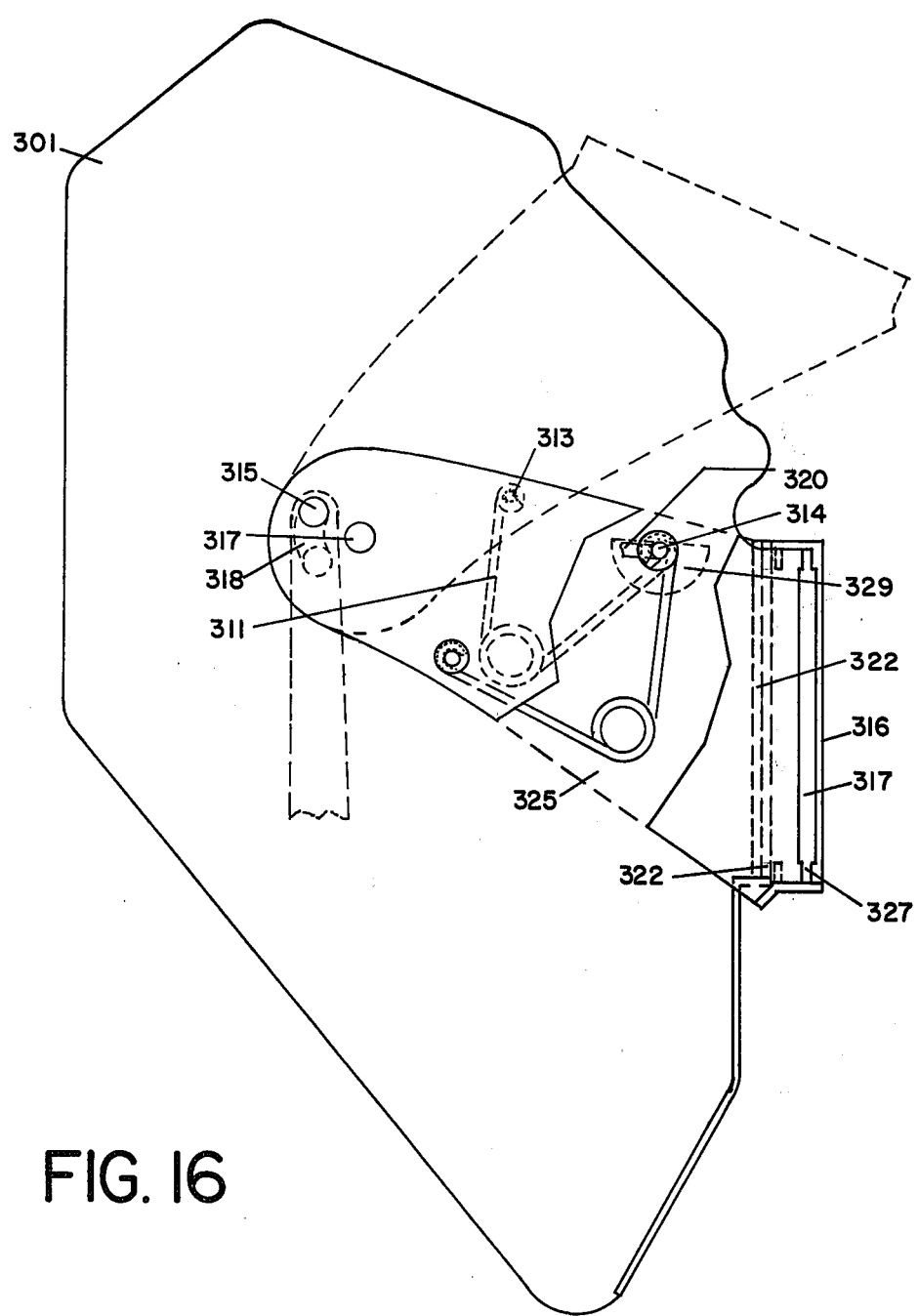
FIG. 16 is a side elevational of a modified helmet with a portion of its visor broken away for showing therebehind a spring mounted in an adjustable slot for varying the spring pressure that holds the visor in an upper position, an upper position of the visor and a corresponding position of the spring being shown in dotted lines, an upper portion of one of the sides of the chin strap being shown in dotted lines.

In FIG. 16 is shown an improvement useful with helmet using either a standard viewing window or a wide angle viewing window.

FIG. 16 is a side elevation of the face shield shown at 301 with the visor in the lowered position but with a cutaway section at 325, allowing a spring which is between the face shield and the visor to be shown.

In FIG. 16 at 301 is the face shield and the visor in lowered position is indicated at 316, and the visor is shown in a raised position in dotted lines at 339. When pressure is applied by the operator to the chin strap 324 a downward pressure is applied to the visor at 315 through a connecting bolt extending through the visor, then through a slot in the face shield at 318 and through a hole in the chin strap.

The weight of the visor and the additional pressure of spring 326 tend to hold the visor closed. The spring 326 pivots on a bolt which passes through a slot in the face shield 320. This bolt is locked in a position by bolt 314 but can be adjusted to any position along the length of the slot 310 to alter the tension of the spring and thus alter the pressure necessary to move the visor upward or downward from the raised position.

The moveable end of the spring is fastened to the visor at pivot bolt 312. The spring is made so that it exerts an outward force, pushing the two ends farther apart. When chin pressure is applied, the visor pivots around point 317, the front of the visor begins to move upward and the two ends of the spring are forced closer together.

When the visor has raised to a position where the clear viewing window is completely exposed, the spring reaches a point where points 317, 312 and 314 are in alignment. At this point the spring is on dead center and has no effect on the visor. If the chin pressure is relaxed at this position the visor will return to the lowered position. However, if additional pressure is applied, the visor will move upward, the spring will begin to exert an upward pressure on the visor as point 312 moves above a line drawn through points 315 and 314.

This pressure is strong enough to hold the visor firmly in the fully raised position until the operator either nods his head in a quick forward motion or pushes the visor downward with his hand. The slot 320 is provided so that the pressure of spring 326 can be altered to accommodate different operators, different types of welding plates and different welding positions.

The spring can be adjusted so that it will close the visor firmly even in an upsidedown position and still allow the operator to open the viewing window. This makes the helmet adaptable to both the operator who welds in a normal position and desires a minimum of chin pressure to operate the visor and to the operator who may find it necessary to weld in any conceivable position, though he will need a little more chin pressure to actuate the visor.

An additional feature is a plate shown at 329 which covers the open portion of slot 320 regardless of the position of bolt 314. It sets on the inside of the face shield and bolt 314 passes through it.

The over-center spring lock has been shown as being used only on one side, but it could be used on both sides of the face shield to even the pressure on the visor if necessary.

Figure 17:
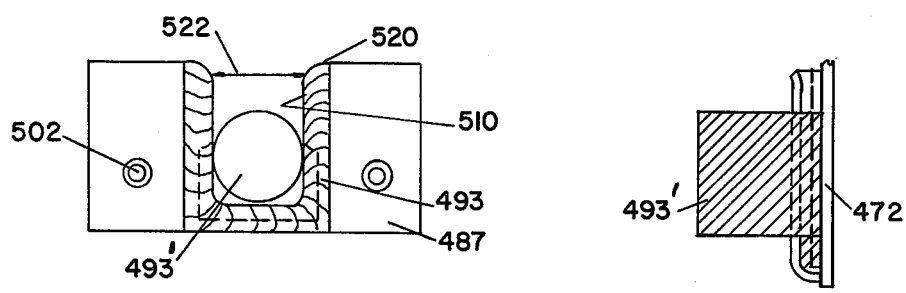
FIG. 17 shows a modified holding device for holding a helmet mounting device, all as seen from the inner side of the helmet, not shown.
Figure 18:
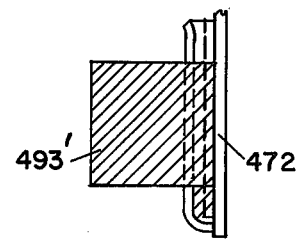
FIG. 18 is a view of the parts of FIG. 17 as it would be seen in a cross section taken vertically through the center of FIG. 17 along the axis of the helmet mounting device.

FIG. 17 shows an improved holding device. No. 487 is a plate which has a raised portion shown as 520 and by the curved shade lines. This allows the helmet mounting device 493' to be inserted from the top with the flange 493 resting under shoulder 520. It is held in place by making the throat 522 slightly narrower than the circular portion of the mounting device 493'. When the mounting device 493' is inserted or removed, the shoulder at 510 must bend slightly to allow the movement. This effectively holds the mounting device in position. Another view is shown in FIG. 18 where 472 represents the band or hard cap on which the mounting device is to be used.

Figure 19:
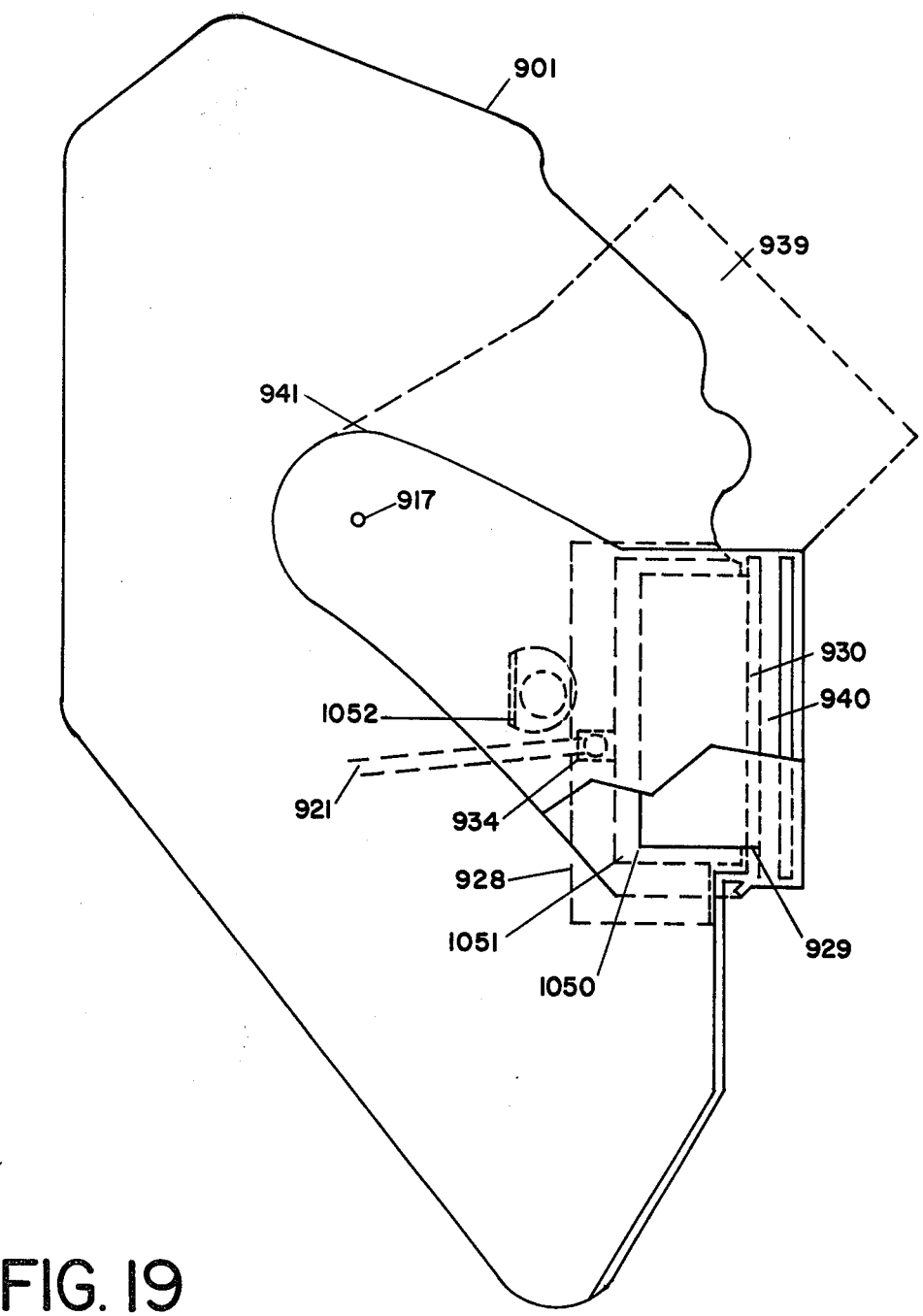
FIG. 19 is a side view of a further modification of the helmet with the visor in place as shown in full lines and in an upper position as shown in dotted lines, the modification providing a wide angle or field of vision by providing for the conventional front opening to be modified so as to extend rearwardly along the sides of the hood in what could be called a "bay-window" helmet.

FIG. 19 shows a hood redesigned to accommodate a "bay window" type clear protective shield. No. 941 is the visor, 901 is the helmet body, 917 is the visor pivot point, 940 shows the position of the dark welding plate, and 929 is the opening in the forward portion of the helmet which has now been extended rearward to 1050. No. 1051 is a line showing the outer limit of protective shield, 930. No. 928 is the retaining frame which holds the clear protective shield in place and 1052 is a retainer which locks the frame in place. One of these retainers is used on each side of the helmet. Adjusting band, 921 is anchored to frame 928 by passing through a slot in the retaining frame at 934. Dotted line, 939 shows the visor in the raised position allowing full vision through the clear protective shield.

Figure 20:
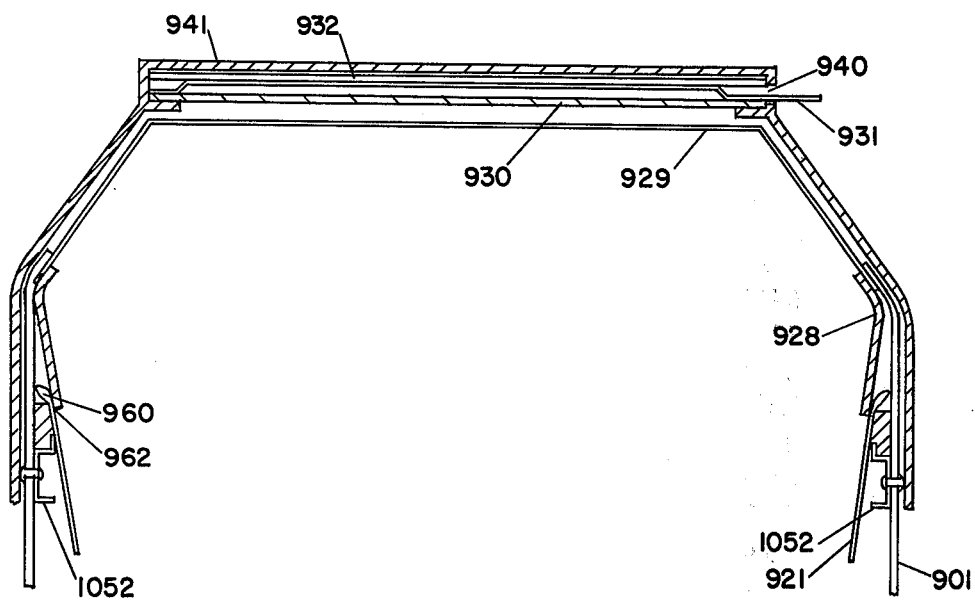
FIG. 20 is a cross-sectional view looking downward on the forward portion of the visor of FIG. 19 as seen in a horizontal section. The section is taken along the line 20—20 of FIG. 19.

FIG. 20 is a cross section view looking downward on the front portion of the visor. 941 is the opening. No. 932 is the front protective clear shield, 930 is the dark welding plate and 931 is the retainer which slips between the two plates after they are inserted through slot 940. No. 929 is the new "bay window" protective shield held in place by frame 928 which is in turn held in place by retainers 1052. No. 901 is the helmet body. No. 921 is the adjusting band which passes through slot in retaining frame at 962.

Figure 21:
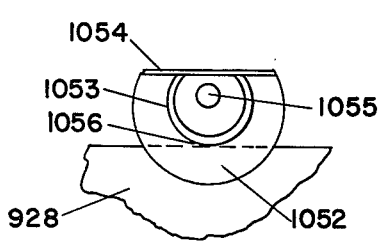
FIG. 21 is a view of a portion of the clear protective shield-retaining frame and of a locking device attaching the the retaining frame to the helmet body shown as the parts would be seen along the line 21—21 of FIG. 20 from the innerside of the helmet, but with these parts rotated 90° clockwise to reach the position shown in FIG. 21.
Figure 22:
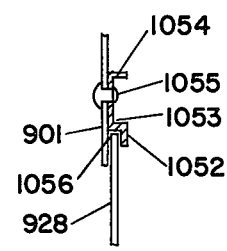
FIG. 22 is a right end elevation of the portions of the helmet shown in FIG. 21.
Figure 23:
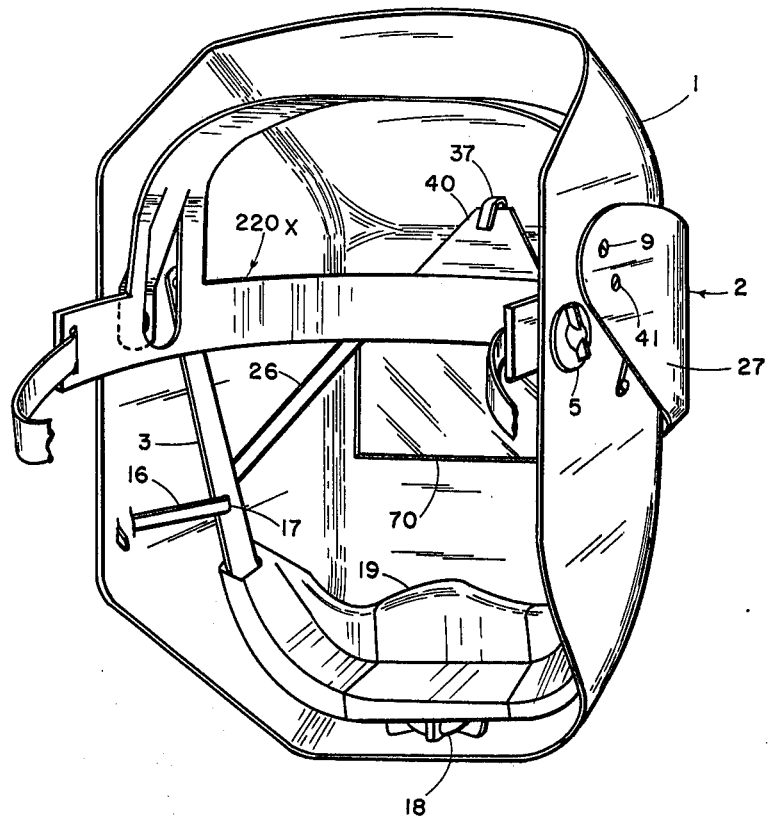
FIG. 23 is a perspective view from the right rear of the main modification of the helmet with the visor down as shown in FIG. 1 except shown in FIG. 23 with a different head band of a modification not claim.

In FIG. 21, a frontal view and a cut away view are shown of the lock which holds the retaining plate, 928. No. 1054 is a portion of the locking device bent at a 90° angle to allow the operator to turn the entire lock in a rotary motion. Since the lock is an eccentric, this tends to allow the lock to move away from the frame at 1056 and allows the frame to be removed. No. 1055 is a rivet extending through the lock and the helmet body with enough tension to hold the lock in place until the operator wishes to move it. No. 1053 shows an offset in the lock which forms a shoulder to retain the frame, 1028.

I claim:

1. A welding helmet comprising a face protective hood having a concave rearward side for receiving an operator's face, means for attaching said hood to the upper portion of the head of said operator, said hood having a forward side having a viewing opening therethrough in a position for being in front of the eyes of said operator while said hood is fixed to the operator's head by said attaching means, a light-filtering module, said module having as at least one of its sections a transparent dark plate for disposition in a covering position for filtering light passing through said opening toward the rearward side of said helmet, means movably mounting said module on said hood so that said dark plate is at times in said covering position and at times in an uncovering position for uncovering at least a substantial portion of said viewing opening, a module controller inside of said concave rearward side of said hood, said module controller being operatively correlated with said module and being adapted to be engaged by the jaw of said operator so that by moving his jaw said operator can cause said module controller to move said module so as to move said dark plate between said covering and uncovering positions, said module controller comprising a chin strap assembly on the rearward side of said hood, said chin strap assembly having a lower chin-engageable portion below said viewing opening and extending generally horizontally from right to left, said chin strap assembly having right and left side portions extending upwardly from its said lower chin-engageable portion, visor-strap connecting means attaching at least one of said chin strap assembly side portions to said light-filtering module so that as said lower chin-engageable portion of said strap assembly is caused to move in one direction said module will move to cause said dark plate to uncover at least a substantial portion of said viewing opening, said module and said strap assembly defining a module and strap combination assembly, said module and strap assembly forming a module-strap component, said light-filtering module comprising a visor having a forward portion and left and right rearwardly extending portions which latter are disposed alongside the left and right sides of said helmet respectively, pivot connection means attaching said right and left sides of said visor to said hood, said dark plate comprising a forward portion of said visor, when in a position for maximum uncovering of said viewing opening, said visor being disposed so that a substantial portion of said dark plate is upwardly of said viewing opening, said hood-to-head attaching means having a head-opening therein for receiving the head of an operator, said head opening having a head-engaging surface for engaging the head of the operator, said means for attaching said hood to the upper portion of the head of said operator comrising head band means defining a substantially horizontal band and right and left pivot attachment means attaching said head band means to said hood in a manner for the pivoting of said hood about said head band upwardly and downwardly about a horizontal axis so that the lower end of said hood can be swung upwardly until at least the majority of said hood is disposed above said pivot connection axis, a stop means for stopping said hood from pivoting downwardly about said axis beyond a position in which said viewing opening is lower than said head band and in a position for sight therethrough by said operator, said stop means having two cooperative parts, one part being mounted on said hood and one part on said head band.

2. The welding helmet of claim 1 in which said chin strap assembly causes said uncovering of said viewing opening at times when said chin strap assembly is pushed downward, having said module and said strap assembly defining a module and strap combination assembly, and resilient closing means interconnecting said module and strap assembly and said hood in a manner urging said module to move into said closing position when downward pressure on said chin strap is released, pivot connection means attaching said right and left sides of said visor to said hood and being disposed more than one-fourth the distance of the forward side of the hood to the rearwardmost part of said head engaging surface, said dark plate comprising a forward portion of said visor, at least one of the side portions of said visor having a portion extending rearwardly from its pivot connection to said hood, an upper portion of one of said chin straps being disposed on an inner side of said hood adjacent said rearwardly extended portion of said one side portion of said visor, and visor-to-chin strap pivot connection means connecting said rearwardly extending portion of said visor with said one chin strap, and pivot clearance opening means in said hood surrounding said visor-to-strap connection means so that said strap is free to move upwardly and downwardly for causing upward and downward movements of said visor so as to make possible said covering and uncovering movements of the dark plate portion of said visor.

3. The welding helmet of claim 1 in which said hood is balanced with respect to said pivot connection axis so that when said hood is disposed in the said upper position it will balance in that position so as to maintain itself conveniently out of the operator's way during times of non-use.

4. The welding helmet of claim 1 in which said pivot attaching means comprises hood mounted bearing portions mounted on the inner side of said hood on the right and left sides thereof around said pivot axis and further comprises band-mounted bearing portions mounted on said band and engaging said hood-mounted bearing portions respectively, and hood-to-band adjustable tension bolt means on the right and left sides of said helmet pressing the respective bearing portions together with adjustable pressure for the adjustable regulation of the amount of frictional force available for holding said hood in an upper position with its normally lowermost portions projecting forwardly from said pivot axis.

5. The welding helmet of claim 1 in which said forward portion surrounds said viewing opening at times when said visor is in said covering position, said forward portion of said visor frame having a dark plate opening therethrough, said forward portion of said visor frame having a dark plate removal slot disposed at one side of said dark plate opening and extending through a side portion of said visor adjacent to the forward portion of said visor whereby a dark plate can be inserted through said dark plate opening behind said forward portion of said visor for covering said dark plate opening in a manner such that said dark plate can be removed and replaced, and dark plate holding means mounted on the rearward side of said forward portion of said visor and lapping at least some side portions of said dark plate for holding said dark plate in a position on said visor for covering said dark plate opening.

6. The welding helmet of claim 1 in which said visor has a forward portion extending across said viewing opening and having visor side frame portions at the right and left sides of said visor, pivot attachment means attaching said side portions to said visor for the pivoting of said visor upwardly and downwardly at its forward side, said hood having an indentation in a portion thereof disposed a substantial distance above said viewing opening for receiving the forward portion of said visor when said visor is in an upward position, said visor receiving indentation extending rearwardly into the forward side of said visor.

7. The welding helmet of claim 1 including a spring attached to said hood at one end and attached to said visor at its other end with the attachment to said visor being disposed rearwardly of the spring attachment to said hood and with the attachment to said visor being disposed above a line between the first end of said spring and said visor pivot axis at times when said visor is in an upper position of an uncovering nature, said connection of said other end of said spring to said visor being disposed below a line between the connection of said first end of said spring to said hood and said visor pivot axis at times when said visor is in a non-rest position lower than said upper position of said visor, said spring making a pressure on said visor at the connection of said second end of said spring of said visor for urging said visor upwardly when said connection of said second end of said spring is above said line and a pressure urging said visor downwardly whenever said connection of the second end of said spring to said visor is disposed below said line.

8. The welding helmet of claim 1 in which said module control comprises a chin strap assembly on the rearward side of said hood, said chin strap assembly having right and left side portions having top sections extending upwardly in said helmet and having lower sections extending from connection to respective side sections inwardly and in lapping relationship with respect to each other one above the other, said inwardly extending strap portions each having a ratchet wheel slot therein, one of said inwardly extending portions having teeth extending from right to left along a forward side of its ratchet wheel slot, the other of said inwardly extending portions having teeth extending across the rearward side of its ratchet wheel slot, and a ratchet wheel assembly comprising a ratchet wheel disposed in said ratchet wheel slots and having teeth disposed in engagement with the said teeth of each of said inwardly extending portions, ratchet wheel mounting means disposed above said ratchet wheel and above said inwardly extending strap portions and adapted to be engaged by the underside of the operator's chin when wearing said helmet, said ratchet wheel mounting means having track-way means therein slidably receiving said right and left sides of said strap assembly, ratchet wheel rotating means rotatably attached to said ratchet wheel and manually operable for the rotation of said ratchet wheel to draw the inwardly extending portions of said right and left side portions of said strap assembly inwardly past said ratchet wheel to various extents so as to make the total length of said strap assembly adjustable without the necessity of upward and downward movement of the side portions of said straps so as to adjust to welders faces of different sizes.

9. The welding helmet of claim 1 in which resilient means is operatively correlated between said hood and said chin strap assembly for urging said chin strap assembly rearwardly.

10. The welding helmet of claim 1 in which said chin strap assembly has a stiffening portion of greater rigidity than the majority of the upwardly extending portions of said chin strap assembly, said stiffening portion extending from right to left across a substantial portion of the lower part of said chin strap assembly.

11. The chin strap assembly of claim 10 in which an upwardly extending forward wall of substantial rigidity is secured to said strap stiffener and extends upwardly from lowermost interior parts of said stiffener assembly a substantial distance for engaging the forward side of the chin of an operator so as to assist in the positioning of the strap assembly against the operator's chin and for preventing the strap assembly from coming off of the forward part of the underside of the operator's chin.

12. The welding helmet of claim 11 in which a resilient means is operatively correlated between said chin strap assembly and said hood and urges said chin strap assembly rearwardly so as to force said forward wall against the operator's chin with a light and comfortable pressure.

13. The welding helmet of claim 9 in which said means rearwardly uring said chin strap assembly is a resilient band fixed to said chin strap assembly at one portion of the band and extending rearwardly with the rearward end of the band attached to a side of said hood.

14. The welding helmet of claim 13 in which said band is adjustably connected to said hood so that it has a free portion disposed between its connection to the hood and said chin strap assembly whereby said free portion of said band is of a variable length.

15. The welding helmet of claim 13 in which said band is adjustably connected to said chin strap assembly for varying the length of that portion of said band which is located between said chin strap assembly and said connection of the rearward end of said band to said hood.

16. The helmet of claim 15 in which said connection of said band to said chin strap assembly comprises an opening in said chin strap assembly extending from right to left through one of the side portions of said chin strap assembly, the walls of said opening receiving said band therethrough sufficiently tightly as to tend to grip said band for holding said band gripped portion and said chin strap assembly in a fixed relationship with each other and whereby a pulling of said band through said opening in said chin strap assembly with a greater force than normally applied by the operator's chin during helmet operation will alter the position of the chin strap assembly on said band for adjusting the length of that portion of said band which is located between said chin strap assembly opening and that rearward portion of said band which is fixed to said hood.

17. The welding helmet of claim 16 in which said band has a forward portion extending from said opening forwardly, means connecting the forward end of said band to an adjacent side of said hood, said band extending in one piece through said opening in said chin strap assembly from its forward portion to its portion that is rearwardly of the chin strap assembly whereby the forward portion of said band holds said chin strap in position against excessive movement rearwardly and yet said opening in said chin strap assembly serves as an adjustable connection adjusting the position of said chin strap assembly along said band with respect to both ends of the band.

18. The helmet of claim 1 which is further provided with resilient means interconnecting said chin strap assembly and a portion of said hood and restraining said chin strap assembly from undesired excessive movements rearwardly with respect to said hood.

19. The welding helmet of claim 1 in which the length of said chin strap assembly is variable so that the height of its lower chin-engageable portion with respect to the remainder of said hood is variable.

20. The welding helmet of claim 19 in which said chin strap assembly is made variable by means of the following construction: the right and left sides of said chin strap assembly having upper portions extending downwardly and having lower portions which overlap each other and which extend inwardly from the sides of said hood, said lower portions of said chin strap assembly each having a slot therethrough and extending vertically therethrough, a forward wall of one of said chin strap slots having teeth in a row thereon extending from right to left so as to serve as a rack, the other of said chin strap assembly slots having teeth on its rearward wall of a similar description, a pinion disposed extending through each of said slots and engaging each of said rows of rack-teeth on respective walls of said slots, a stiffening member disposed above said lower portions of said straps, a pinion hand-control member fixed to said pinion and extending downwardly from said pinion and means rotatably mounting said pinion and said handcontrol member rotatably on said stiffener so that as said hand-control member is rotated in each of two opposite directions, said lower portions of said straps will be drawn into greater or lesser overlapping respectively for adjusting the total length of said chin strap assembly, and means slidably attaching said right and left chin strap portions to said stiffener member.

21. The welding helmet of claim 1 having said chin strap assembly having right and left side portions extending upwardly from its said lower-chin engageable portion, means attaching at least one of said chin strap assembly side portions to said light-filtering module so that as said lower chin-engageable portion of said strap assembly is caused to move in one direction said module will move to cause said dark plate to uncover at least a substantial portion of said viewing opening.

22. The welding helmet of claim 21 in which said chin strap assembly causes said uncovering of said viewing opening at times when said chin strap assembly is pushed downward, having said module and said strap assembly defining a module and strap combination assembly, and resilient closing means interconnecting said module and strap assembly and said hood in a manner urging said module to move into said closing position when downward pressure on said chin strap is released, a visor spring is provided connecting said visor to said hood, said visor spring being substantially of a V-shape and having a first end connected to said visor at a side portion thereof and a second end connected to said hood, said connections to said hood and said visor being in a position such that when said visor is open, said visor spring will tend to hold said visor open.

23. The welding helmet of claim 22 in which said ends of said visor spring are also positioned for holding said visor in its position for accomplishing the holding of said dark plate in said covering position at times when said visor is in said latter visor position.

24. The welding helmet of claim 1 having switch means contacts on said module and on said hood respectively which are in contact with each other when said dark plate is in said closing position, an arc welding assembly having a power source, and electrical circuit means interconnecting said power source and said welder only when said switch contacts are engaging each other so that welding cannot be done unless said dark plate is in said closing and eye-protection position.

25. The welding helmet of claim 1 having said attaching-to-head means and said hood comprising a hood and head attachment means having a first stop part on said hood and a second stop part on said head attachment means.

26. The welding helmet of claim 1 having said attaching-to-head means comprising a hard cap.

27. The welding helmet of claim 1 having said view opening having walls concave in top plan view on their rearward sides and extending around substantial portions of the right and left sides of said hood to provide a bay window effect for wide angle viewing.

28. The welding helmet of claim 1 having a clear plate disposed across the backside of said view opening and covering said view opening, and a retainer on the rearward side of said clear plate, and releasable lock means attaching said hood and retainer together for holding said retainer in a position for holding said clear plate in said position across said viewing window.

* * * * *